United States Patent [19]

Sluss et al.

[11] Patent Number: 4,652,450

[45] Date of Patent: Mar. 24, 1987

[54] BACTERIAL FSH BINDING INHIBITOR

[75] Inventors: Patrick M. Sluss, East Greenbush; Leo E. Reichert, Jr., Loudonville, both of N.Y.

[73] Assignee: Research Corporation, New York, N.Y.

[21] Appl. No.: 646,593

[22] Filed: Aug. 31, 1984

[51] Int. Cl.[4] .......................... A61K 35/74; C12P 1/04

[52] U.S. Cl. ..................................... 424/115; 435/170

[58] Field of Search ................. 424/115, 170; 435/170

Primary Examiner—Jerome D. Goldberg
Attorney, Agent, or Firm—Scully, Scott, Murphy & Presser

[57] ABSTRACT

This invention relates to an FSH-binding inhibitor produced by microorganisms of the genus Serratia.

1 Claim, 6 Drawing Figures

BACTERIAL FSH BINDING INHIBITOR

FIELD OF THE INVENTION

The present invention relates to a substance capable of interfering with hormone activity. More specifically, it relates to an FSH-binding inhibitor produced by a bacterium, Serratia.

BACKGROUND OF THE INVENTION

Follicle-stimulating hormone (FSH) is a gonadotropic hormone secreted by the anterior pituitary in all normal adult male and female mammals, and, in fact, probably in all vertebrates. In the male this hormone functions in the process of spermatogenesis, or sperm formation, by stimulating conversion of primary spermatocytes into secondary spermatocytes within the seminferous tubules. Without the action of FSH, sperm formation cannot proceed normally. In the female, FSH operates by initiating the growth of ovarian follicles and the enclosed ova during the female menstrual cycle. In conjunction with the action of a second hormone luteinizing hormone (LH), it promotes rapid follicular growth to the point of ovulation, or release of the ovum from the ovary. FSH thus plays an integral role in maintaining normal fertility in both males and females.

FSH, a glycoprotein, achieves its desired effect, as do other hormones, by interaction or binding with a receptor in the target cells of the appropriate organs, in this case, the ovaries or the testes. As it is currently understood, with protein or peptide hormones, the receptor is probably a membrane-localized macromolecule which recognizes the hormone in a particular way and activates the cell to initiate the appropriate biological response. Whatever the mechanism of action, it is known that interference with the binding of the hormone to the receptor will result in the prevention of the expression of the hormone's usual effect. Therefore, it is possible to control the action of FSH by preventing its binding to its receptor, thus interfering with normal fertility by disrupting the usual course of spermatogenesis or ovulation.

Substances which are capable of inhibiting the binding of FSH to its receptor have been reported from a number of sources. Such inhibitors have been found in bovine follicular fluid (Darga, N. S. and Reichert, L. E., Jr. *Adv. Exp. Med. Biol.* 112: 383-388, 1977; Fletcher, P. W. et al., *Mol. Cell. Endocrinol.* 25: 303-315, 1982); human serum (Sanzo, M. S. and Reichert, L. E., Jr., *J. Biol. Chem* 257: 6033-6040, 1982) and seminal plasma (Dias, J. A. et al., *J. Androl* 5: 259-268, 1981). All of these substances are of low molecular weight (less than 1000), and neither the origin nor the identity of any of them is well-understood.

A new FSH-binding inhibitor has now been isolated. The inhibitor in question is readily distinguished from earlier known inhibitors by its much higher molecular weight (greater than 6,000), and a number of other chemical features. It is also unique in that it has been identified from a microbial source, the bacterium Serratia. This novel binding inhibitor has potential use as a contraceptive agent as well as a reagent in the study of FSH-receptor interactions and in purification of the FSH receptor.

BRIEF DESCRIPTION OF THE INVENTION

The present invention relates to an FSH-binding inhibitor characterized by the following features:
 (a) a molecular weight of over 6000;
 (b) inactivation by heating for 30 minutes at 60° C.
 (c) inactivation by pH below 4;
 (d) insolubility in ether, 75% acetone or 40% ammonium sulfate; and
 (e) solubility in 80% ethanol; and
 (f) absence of serine protease activity; said binding inhibitor being derived from a microorganism of the genus Serratia.

The present invention also provides a method for the production of the FSH binding inhibitor which comprises inoculating a suitable culture medium with a microorganism of the genus Serratia incubating the inoculated medium for a period of time and under conditions suitable for the production of said inhibitor, and recovering the inhibitor.

A: Levine #33; B: beta-hemolyhic Streptococcus; C: Pseudomonas sp.; D: *Pseudomonas maltophilia;* E: TSB #34; F: Serratia 5107763; G: Levine #11; H: Serratia 5107763; I: Control=sterile PFF.

Figure 3:
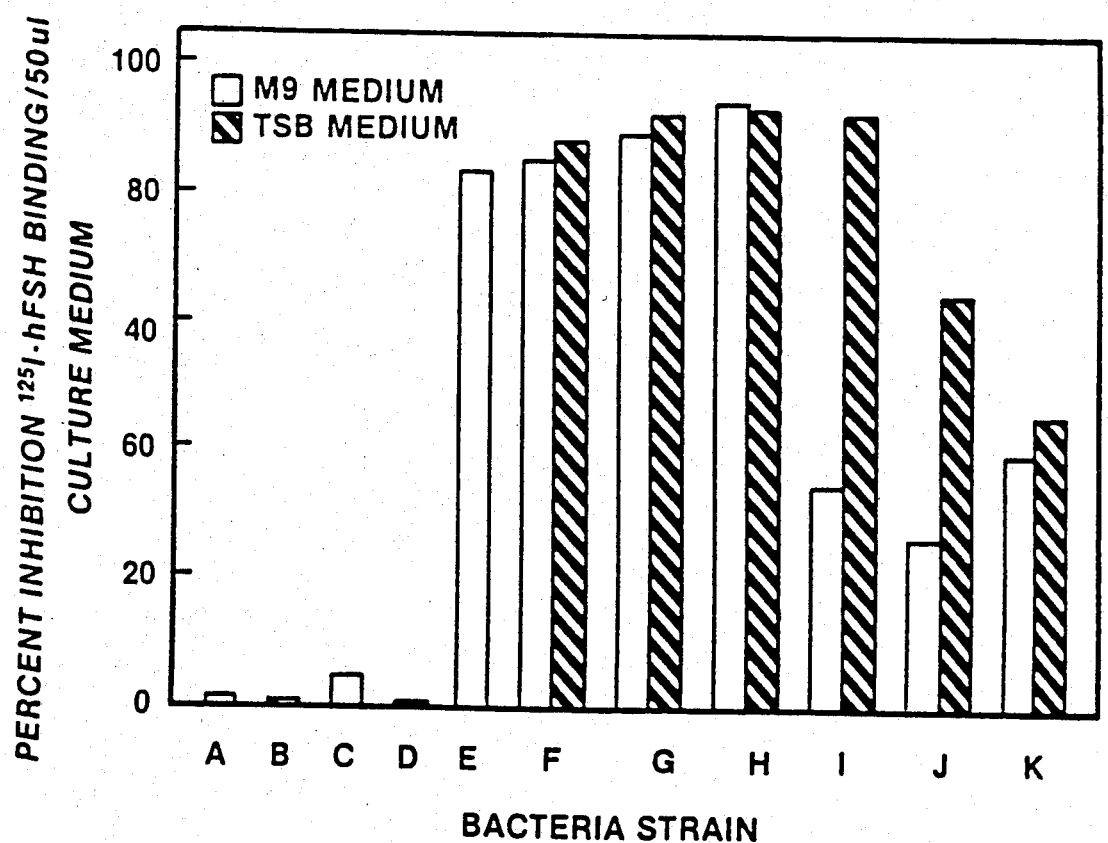

FIG. 3 shows a comparison of FSH-BI production between different strains of Serratia.

Figure 4:
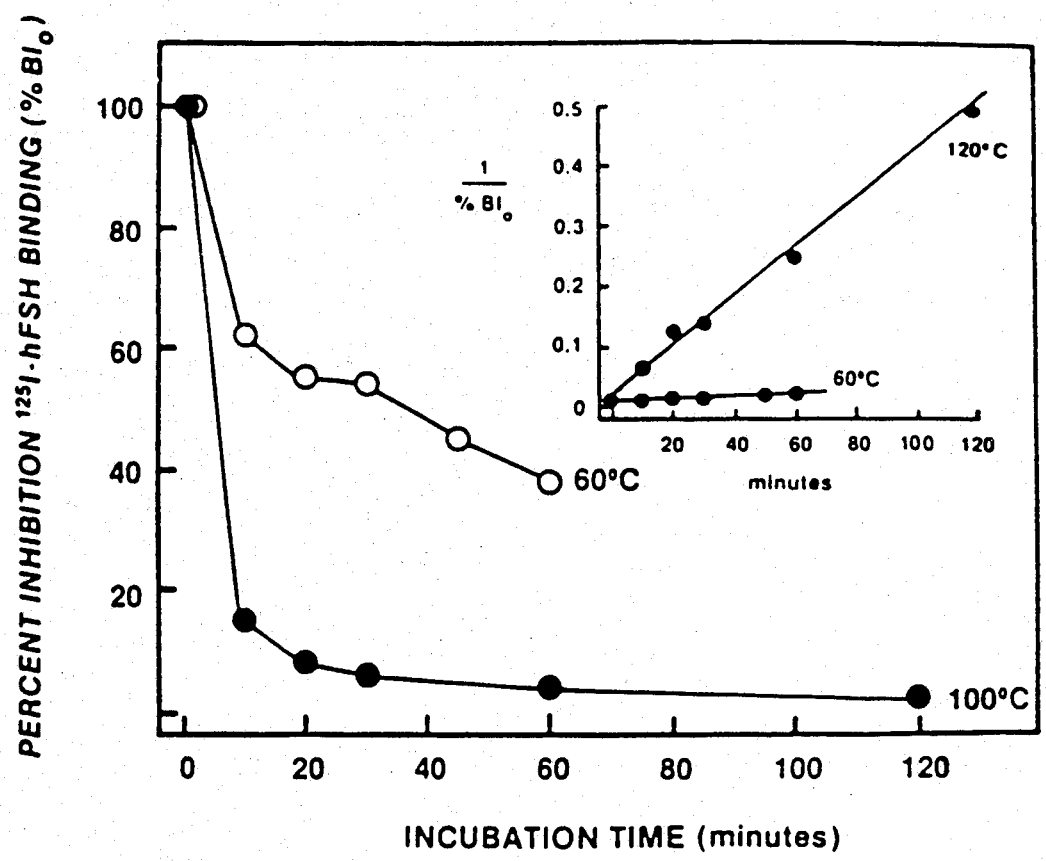

FIG. 4 depicts the results of FSH-BI heat sensitivity testing.

Figure 5:
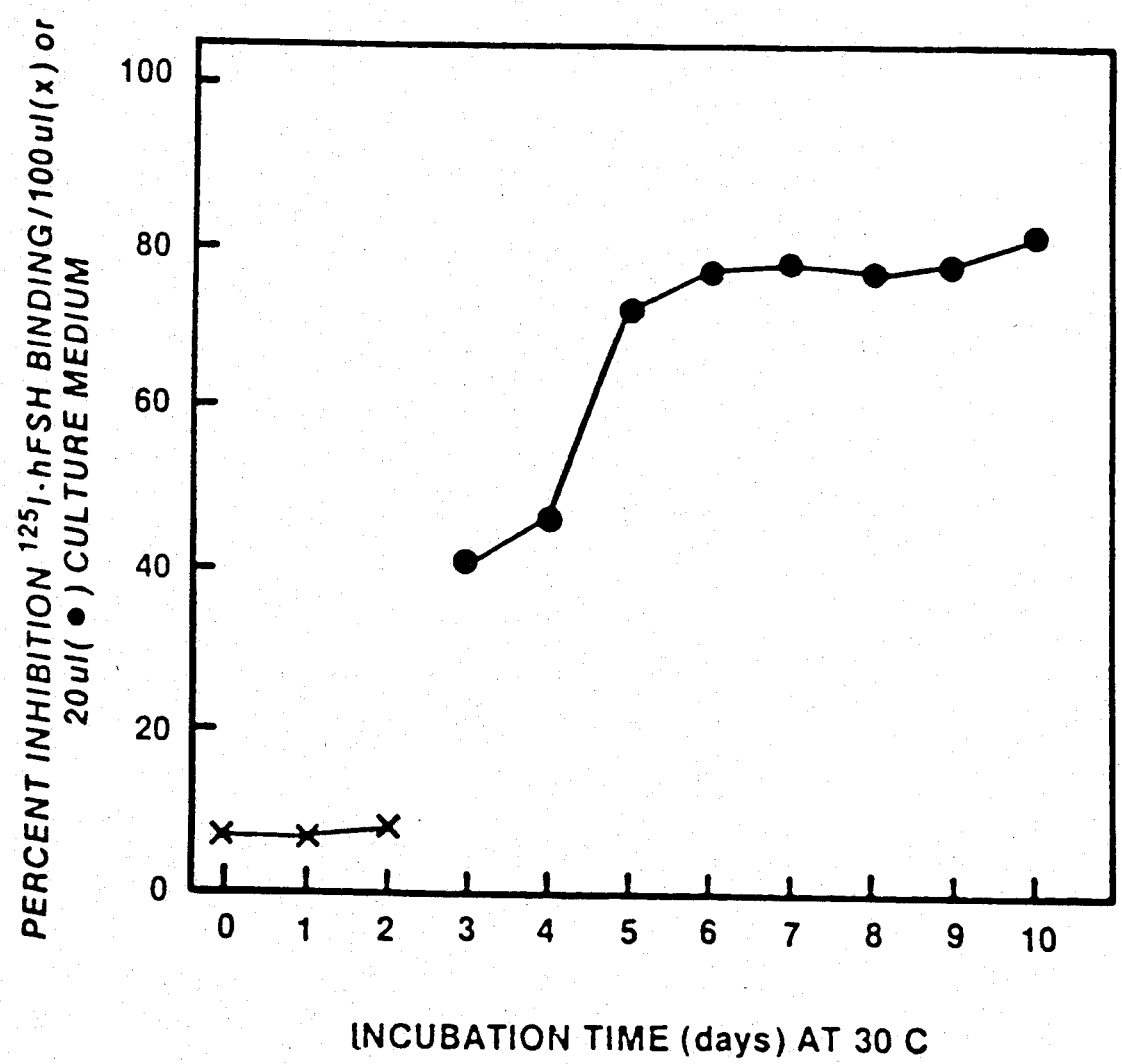

FIG. 5 shows FSH-BI production by Serratia 5107763 in M-9 medium.

Figure 6:
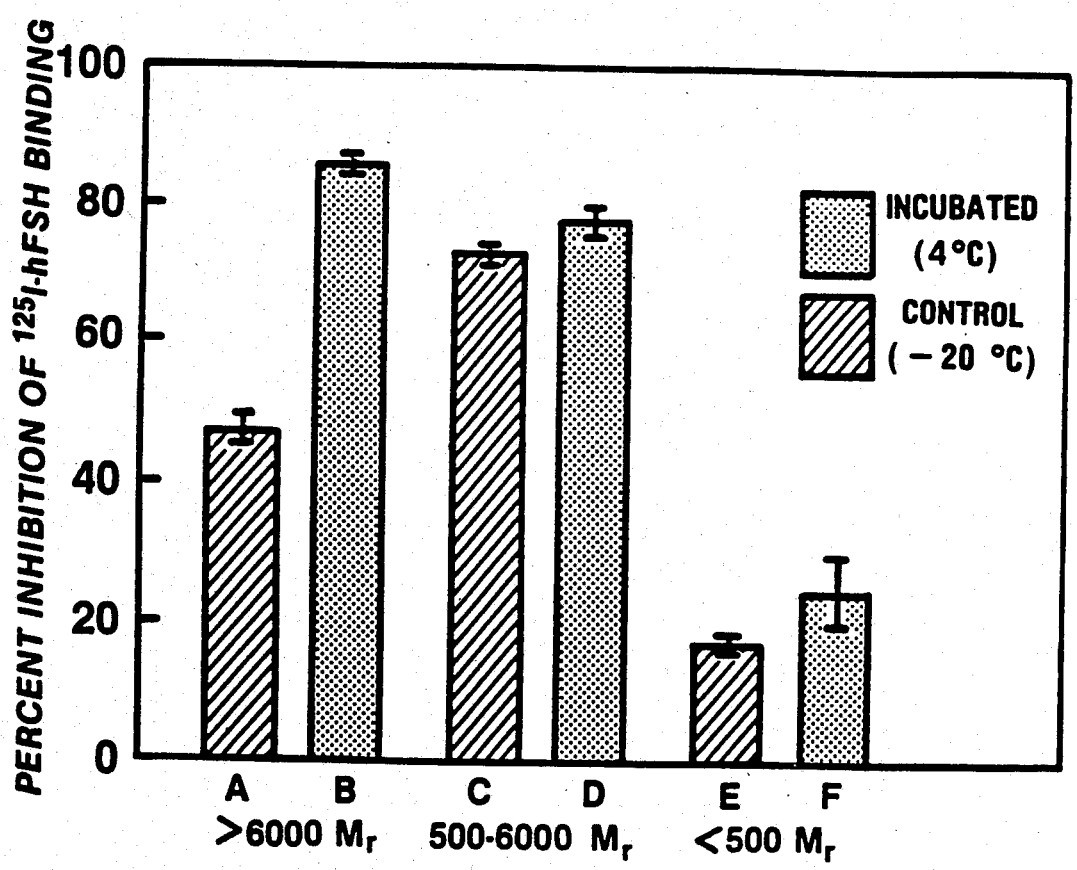

FIG. 6 demonstrates the activity of follicular fluid fractionated using membrane dialysis and ultrafiltration. Columns A, C, and E refer to FSH-BI activity of PFF fractions stored at −20° C. for 11 days; columns B, D, and F refer to corresponding fractions of PFF incubated at 4° C. for 11 days.

DETAILED DESCRIPTION OF THE INVENTION

The FSH-binding inhibitor (FSH-BI) of the present invention was originally detected in porcine follicular fluid which was contaminated by bacteria. Initial experiments to pinpoint the exact source of the inhibitory activity in the fluid showed that when the PFF was incubated at temperatures conducive to bacterial growth, the activity of the FSH-BI increased dramatically, indicating the bacterium was the source of the inhibitory activity. Further attempts at characterization of the inhibitor showed that it was of fairly high molecular weight, differentiating it from the low molecular weight substances previously described from various follicular fluids.

Experiments performed to determine which of the contaminating bacteria isolated in pure culture from the porcine follicular fluid showed that the responsible bacterium was a species of the genus Serratia (Example 1). The particular strain present in the contaminated fluid was Serratia biotype 5107763; the biochemical features characteristic of this biotype indicate that this is probably a strain of *S. liquefaciens*. However, additional experiments (FIG. 3) with a variety of species of Serratia obtained from the American Type Culture Collection show that the phenomenon of production of FSH-binding inhibition is found in a number of different species of the genus (Example 2). These data support the assumption that this is a property of the genus Serratia as a whole. Whether any particular isolate is capable of producing FSH-BI is easily determined by the skilled artisan by the mere expedient of performing the test described herein utilizing different strains of Serratia.

Analysis of the chemical properties of the FSH-BI shows a number of identifying characteristics (Example 3). Stability testing at various times and temperatures indicates that the inhibitor is heat labile, with a rapid loss of activity occurring after brief heating at both 60° C. and 100° C. Lyophilized material retains constant activity, however, when stored for up to 2 months at −20° C. The bacterial inhibitor is also shown to be sensitive to a low pH since significant activity is lost at a pH of 4 or lower. It does not, however, appear to be significantly affected by relatively high pH (Table 1).

Solubility studies (Table 1) further show that the FSH-BI is insoluble in ether, 75% acetone and 40% ammonium sulfate. It, however, soluble in 80% ethanol, although 50% of its activity appears to be lost in ethanol, presumably due to its inactivation. Membrane filtration analysis shows that the substance in question has a molecular weight of over 6000. Tests used to determine whether the inhibition observed was connected with proteolytic activity of the inhibitor show that the material exhibits no serine protease activity (Example 3).

The culturing of Serratia for the production of FSH-BI can be performed on virtually any type of medium containing a suitable carbon source. A wide variety of different media such as TSB, Ham's F12 and thioglycolate Fluid Agar have been successfully employed to produce FSH-BI from Serratia. Even minimal media, such as M9, with only glucose as carbon source has been sufficient to allow production of the inhibitor (FIG. 5, Table 2). It is within the knowledge of the skilled artisan to determine the conditions of incubation best suited for the particular strain of Serratia being employed. Recovery of the FSH-BI inhibitor may be accomplished by any number of traditional recovery methods well-known in the art, such as filtration, ether, extraction, acetone or ammonium sulfate precipitation, among others.

Figure 1:
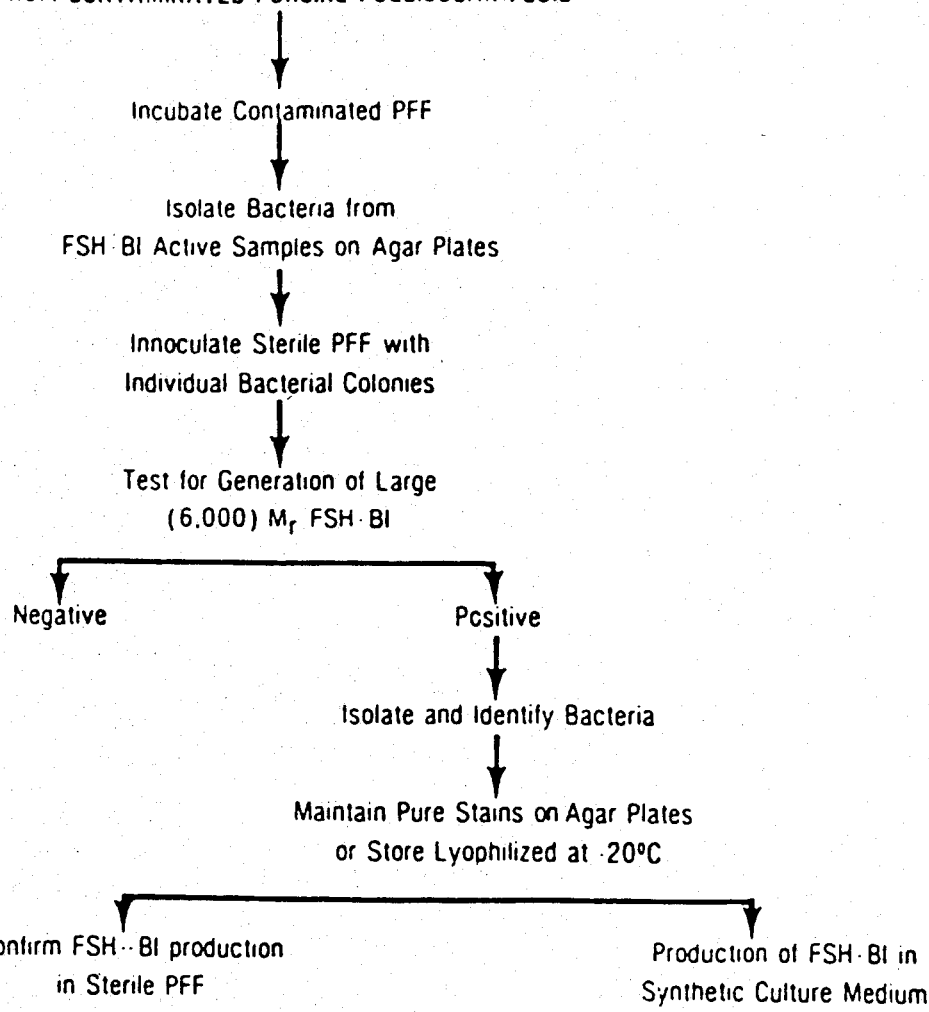
FIG. 1 outlines the procedure followed for the isolation of Serratia and FSH-BI.

The bacterial FSH-BI disclosed herein exhibits a high level of inhibition of FSH-binding, as shown in FIG. 1 and Tables 3 and 14; as such it may be useful in the control of fertility, and contraception. It is particularly useful in that it is applicable to a physiological system (i.e., one in which gametogenesis is FSH-dependent) present in virtually all vertebrates, male and female. The in-vitro $BI_{50}$ (dose of material required to give 50% inhibition) of a relatively impure material (about 7% purity) is about 80 ng/ml. The amount of purified FSH-BI required to produce a similar pharmaceutically acceptable level of inhibition may vary but is, generally speaking, between the $BI_{50}$ for the purified material and 10-fold higher. Thus, in the average human, the effective dose range will generally be between 0.5 and 5.0 ug/kg of body weight, depending on the size of the patient to be treated; it will, however, be possible for the physician to vary these doses based on the chosen route of administration and form of inhibitor required.

The subject binding inhibitor also provides a useful research tool in endocrinological studies. For example, it may be used in the process of isolation of FSH-receptor. Because of the method of production of the inhibition it may be produced in amounts sufficient to be linked to solid supports for use as an affinity resin. Such an affinity resin may then be used for purification of the receptor by affinity chromatography and standard liquid chromatography techniques. It may also be used in the study of FSH-receptor interactions, since gram quantities of inhibitor can be produced for use as an FSH analog. Such an analog can be used in the native form, or radioactively labeled for kinetic and structure/function studies of FSH-receptor interactions.

The present invention may be more clearly understood by reference to the following nonlimiting examples:

EXAMPLE 1

Bacterial growth was observed in 5 ml aliquots of PFF incubated at 32° C. for 3 days or at 4° C. for 19 days. Samples of each aliquot were tested for increased FSH-BI relative to PFF stored at −20° C. ("Control"). All of the three replicate aliquots incubated at 4° C. and 2 of the 3 aliquots incubated at 32° C. showed increased activity relative to control PFF. Most of the FSH-BI activity of control PFF was dialyzed through spectrapor #1 membranes ($BI_{50}$=150 to 200 ul before dialysis compared to $BI_{50}$>1 ml after dialysis). In contrast, FSH-BI activity due to bacterial growth was not dialyzable ($BI_{50}$ values were between 5 and 45 ul for incubated samples and were similar before and after dialysis). There were no significant pH differences between incubated and control PFF either before (7.09±0.15) or after (5.59±0.15) dialysis.

Figure 2:
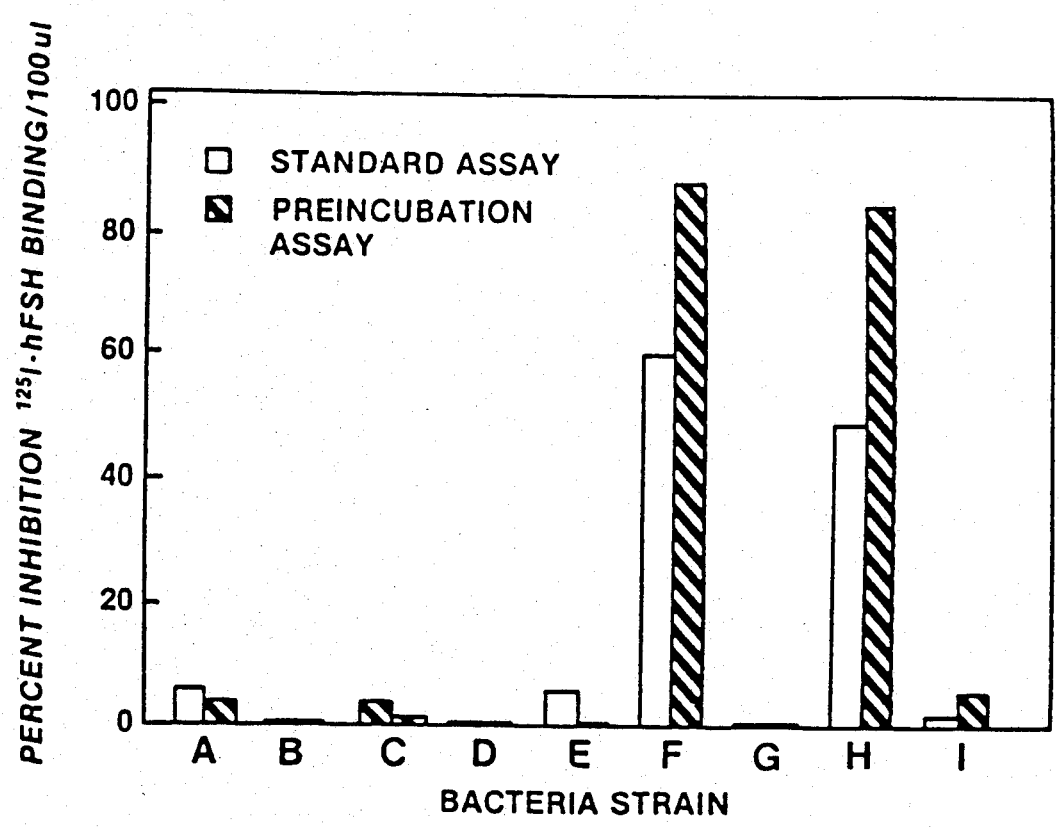
FIG. 2 shows a comparison between FSH binding inhibition of Serratia and other contaminating bacteria isolated from PFF. Pure strains were maintained on Trypticase Soy 15% sheep blood or Levine EMB agar plates.

All three aliquots incubated at 4° C. and the most active ($BI_{50}$=45 ul) aliquot incubated at 32° C. were used to isolate the bacterium responsible for FSH-BI activity according to the procedures outlined in FIG. 1. Bacterial growth was observed on all plates after 24 hours at 30° C. when these 4 samples were plated. Bacteria from a total of 39 individual colonies, taken off both TSAII (Gram+ and Gram− bacteria) and Levine EMB (Gram− bacteria only), were used to inoculate sterile PFF. Inoculated PFF was incubated (30° C. for 24 hours) and tested for increased FSH-BI activity relative to sterile PFF incubated under identical conditions. Samples of PFF showing increased FSH-BI activity were plated on TSAII for maintenance of bacteria and subjected to standard biochemical tests in order to identify the bacteria. Only one of the 39 individual colonies tested was consistently active. Based on a series of standard biochemical test, the bacterium was identified as Serratia species, biotype 5107763. Based on this biotype data the bacterium is considered to be *Serratia liquefaciens* (probability 1/90) although the possibility that they are *Serratia marcescens* (probability 1/229), a closely related species, cannot be ruled out. Three other strains of bacteria were isolated from PFF and identified as beta-hemolytic streptococcus (group C), *Pseudomonas maltophilia* and Pseudomonas sp. None of these were capable of generating FSH-BI in sterile PFF. Results of a typical assay for the generation of FSH-BI in sterile PFF are shown in FIG. 2. Serratia 5107763 was the only bacterium isolated from PFF which was capable of generating non-dialyzable (>6000$M_r$) FSH-BI in sterile PFF. Additionally, as shown in FIG. 2, the FSH-BI potency of PFF incubated with Serratia 5107763 was increased when the samples were preincubated with calf-testis membranes for 2 hours at 20° C. before addition of $^{125}$I-hFSH to the radioligand-receptor assay (hatched bars, FIG. 2). Even under these conditions of increased assay sensitivity, no FSH-BI was detected in samples of PFF inoculated with the other bacteria. Serratia 5107763 was also active, with respect to the generation of FSH-BI activity, after storage in skim milk or Trypticase Soy Broth at −60° C. or after storage at −20° C. after lyophilization. FSH-BI activity generated by Serratia 5107763 under standardized test procedures was quite consistent and was not correlated with measurable changes in the total protein content of PFF after the incubation period.

EXAMPLE 2

The following example illustrates the ability of a number of different types of Serratia to produce FSH-BI. Results of the test are shown in FIG. 3.

Strains of Serratia were obtained from the American Type Culture Collection (ATCC). ATCC strain numbers are identified for each strain of Serratia: F: *Serratia marcescens,* 13880; G: *Serratia marcescens,* 21074; H: *Serratia liquefaciens,* 11367; I: *Serratia liquefaciens,* 27592; J: *Serratia plymuthica,* 183; K: *Serratia fonticola,* 29844. Cultures of these bacteria on TSAII agar plates were used to inoculate 2 ml aliquots of Trypticase Soy Broth or M9 culture medium. After 48 hours at 30° C., bacteria were removed by centrifugation and the media were dialyzed against water. 50 ul aliquots were assayed for FSH-BI using standard assay conditions. Results shown in FIG. 3 represent the mean of duplicate determinations; open bars represent M9 medium and hatched bars represent TSB broth. Sterile M9 and M9 inoculated with bacteria from PFF which did not secrete BI in sterile PFF were used as negative controls: A: beta-hemolytic Streptococcus; B: *Pseudomonas maltophilia,* C: Pseudomonas sp., D: Sterile M9 control; E: Serratia 5107763, isolated from PFF, was included as a positive control. Activity of sterile TSB and TSB inoculated with Serratia 5107763 can be seen in Table 2.

EXAMPLE 3

The following example describes the procedures used in the chemical characterization of the FSH-BI produced by Serratia.

Molecular weight determination:

A sample of porcine FF was divided into two aliquots, one stored at −20° C. for 11 days, the other incubated at 4° C. for the same period. There was noticeable bacterial growth in the fraction incubated at 4° C. for 11 days, whereas no growth was seen in the fraction stored at −20° C. Each sample was then fractionated by dialysis through a Spectrapor #1 membrane, which retained substances of molecular weight 6000 or greater, and diafiltration through an Amicom UM-05 membrane, which retained substances of molecular weight 500 or greater. Each fraction was then assayed for FSH-BI activity. As can be seen in FIG. 6, there was no difference in FSH-BI of the fractions passing through the Spectrapor #1 membrane and retained by the Amicom UM-05 membrane (compare FIG. 6, C and D; molecular weight between 500 and 6000) or the fraction passing the Amicom UM-05 membrane (compare FIG. 6, E and F; molecular weight less than 500). In contrast, the fraction not passing through the Spectrapor #1 membrane on dialysis (molecular weight greater than 6000) and derived from the incubated PFF sample, had an FSH-BI potency significantly greater than the fraction derived from the unincubated sample (compared FIG. 6, A and B). Thus, it seemed clear that FSH-BI being generated by the bacteria was of large molecular weight (retained by Spectrapor #1 membrane on dialysis), i.e. greater than 6000.

Heat Sensitivity:

Aliquots (3 to 5 ml) of dialyzed (Spectrapor #1 membranes) culture medium which had been inoculated with Serratia 5107763 and incubated for 48 hours at 30° C. were placed in 20 ml capped glass vials. This FSH-BI containing medium was heated with constant stirring at 60° or 100° C. in a water bath. Samples (0.5 ml) were removed at various times (t) between t=0 and t=120 minutes. Samples were stored on ice until all samples had been collected. FSH-BI was determined using 50 ul aliquots of samples under standard assay conditions. FSH-BI activity at t=0 was used to normalize the data. FSH-BI in 50 ul at t=0 was approximately 50% for the 100° C. studies and 75% for the 60° C. studies. Points represent means of 2 for 100° C. and 4 determinations for 60° C. Insert shown 1/% BI at time=0 for each data point.

pH Stability of FSH-BI: Lyophilized material from desalted concentrates of culture medium containing FSH-BI was resuspended in 50 mM HEPES, pH 7.0. The pH of individual aliquots was lowered by addition of 10M acetic acid or raised by addition of 10M potassium hydroxide. Acetate and potassium hydroxide were chosen since they affect the assay less than other commonly used ions. After 1 to 2 hours incubation at room temperature, the samples were adjusted to pH 7.2 using either acetate or potassium hydroxide. Samples were then assayed for FSH-BI activity. Untreated FSH-BI containing material was used as a control for activity loss due to pH treatment and sterile culture medium was used for procedural controls. No FSH-BI activity was detected in the sterile culture medium controls which had been treated exactly as the lyophilized culture medium.

Ethanol Solubility of FSH-BI: Cell-free, dialyzed culture medium containing FSH-BI was placed in a glass beaker. The sample was stirred constantly and temperature was maintained at −8° to −° C. in a dry ice/methanol/water bath. Appropriate volumes (measured at room temperature) of pure ethanol were cooled to −40° C. and added dropwise to the sample. Precipitate was removed by centrifugation (30,000×g for 15 minutes at 4° C.), drained completely and resuspended in 50 mM Tris, 5 mM $MgCl_2$, 0.1M Sucrose, pH 7.5 (Rinse Buffer); then flash evaporated for 2 to 3 minutes at 40° C. under vacuum to remove residual ethanol. The final supernate (80% ethanol) was flash evaporated to dryness and the residue was resuspended in Rinse Buffer. Samples in Rinse Buffer or sterile culture medium treated exactly as FSH-BI containing material, were assayed for FSH-BI activity. No FSH-BI activity was detectable in control samples from sterile medium.

Ether Solubility of FSH-BI: Cell-free, dialyzed culture medium containing FSH-BI was placed in a separatory funnel. Ten volumes of diethyl ether was added and the funnel contents were mixed by rotation for 30 minutes at room temperature. Aqueous and solvent layers were allowed to separate and removed individually. Residual ether was removed from the aqueous layer by flash evaporation under vacuum (40° C., 2 to 3 minutes). The solvent layer was evaporated to dryness under nitrogen gas at room temperature and the residue was resuspended in Rinse Buffer. Samples and controls (sterile medium) were assayed for FSH-BI activity. No FSH-BI activity was detectable in control samples.

Acetone Precipitation of FSH-BI: Cell-free culture medium (undialyzed) containing FSH-BI was adjusted to a pH of 4.5 to 5.0 with 10M acetic acid (HPLC grade) and placed in a glass Erlenmeyer flask. Four volumes of cold (4° C.) acetone (HPLC grade) were added and the flask was incubated at 4° C. overnight. Acetone was then decanted and the precipitate (adhered to bottom of flask) was resuspended in Rinse Buffer. Residual acetone was removed by flash evaporation under vacuum (5 minutes at 40° C.). Precipitate from large volumes (500 ml) of culture medium was resuspended in water, shell frozen and lyophilized. Samples and controls (sterile medium) were assayed for FSH-BI which was undetected in controls.

Ammonium Sulfate Precipitation of FSH-BI: Cell-free culture medium (undialyzed) containing FSH-BI was adjusted to a pH of 4.5 to 5.0 with 10M acetic acid. Dithiothreitol (Sigma) and disodium ethylenediamine tetraacetic acid (Sigma) were added to a final concentration of 1 mM each. Appropriate amounts of solid ammonium sulfate (Sigma, Grade III) were added. This solution was stirred constantly at room temperature for 30 minutes. Precipitate was recovered by centrifugation at 30,000×g for 30 minutes at 4° C. Precipitates were resuspended in water, dialyzed (6,000 $M_r$ cut-off Spectrapor #1 membranes) for 24 hours against deionized water, shell frozen and lyophilized. Lyophilized material was resuspended in Rinse Buffer prior to assay for FSH-BI activity, which was undetectable in samples from sterile culture medium controls.

The results of a number of the above tests are summarized in Table 1.

Protease Activity Assay: Samples containing FSH-BI were tested for protease activity using a casein substrate embedded in agar (BioRad, Rockville Center, NY). Briefly, two gel tablets were dissolved in 10 ml water and poured onto 85×65×2 mm plastic diffusion plates (BioRad). After cooling, 4 mm diameter sample wells were punched in the gel. Samples (10 ul) were placed in the wells and the plates were incubated at room temperature for 24 hours. The diameters of clear areas (digestion rings) around sample wells, due to proteolysis of the casein substrate, were recorded at 4 and 24 hours. Sterile PFF or culture medium was used as a negative control and alpha-chymotrypsin (Sigma, St. Louis, MO) was used as a positive control. Area of digestion rings was linearly related to dose of alpha-chymotrypsin from 25 to 100 ng/well. The limit of detection of the enzyme was approximately 5 ng ($2.85 \times 10^{-4}$ IU).

Total Protein Assay: Total protein assay was performed by the Coomassie Brilliant Blue G-250 technique (Bradford, 1976) using an assay kit (BioRad) with bovine serum albumin as the reference standard.

TABLE 1

Solubility of FSH—BI under various conditions and sensitivity of FSH—BI to pH exposure.

| Treatment | Sample 1 | Volume (ul) | % BI[a] | % of initial FSH—BI Activity |
|---|---|---|---|---|
| A. pH Exposure for 2 h at 25° C. then neutralize to 7.2 | pH 7.2 (initial) | 20 | 77 | 100 |
| | 12 | 20 | 74 | 96 |
| | 4 | 20 | 35 | 45 |
| | 2 | 20 | 21 | 27 |
| B. Ether | Initial | 100 | 74 | 100 |
| Extraction: | Solvent layer | 100 | 0 | 0 |
| | Aqueous layer | 100 | 84 | 114 |
| C. Ethanol Precipitation | Initial | 100 | 74 | 100 |
| | 20% ppt | 100 | 3 | 4 |
| | 33% ppt | 100 | 2 | 3 |
| | 50% ppt | 100 | −6 | −8 |
| | 80% ppt | 100 | −1 | −1 |
| | 80% soluble | 100 | 37 | 50 |
| D. Acetone Precipitation | Initial | 100 | 92 | 100 |
| | 75% Acetone ppt | 100 | 96 | 104 |
| E. $(NH_4)_2SO_4$ ppt | Initial | 100 | 92 | 100 |
| | 40% ppt | 100 | 88 | 96 |

[a]mean of 2 to 4 determinations, sterile M9 treated similarly and assayed at the same doses showed no significant inhibition of binding.

EXAMPLE 4

The following example illustrates a typical procedure for culturing of Serratia for the production of large amounts of FSH-BI:

A culture of Serratia isolated from PFF was conducted in 500 ml aliguots of M9 medium [M9 medium is prepared in 2–10 liter batches as follows: 6 g/l $Na_2HPO_4$; 3g/l $KH_2PO_4$; 0.5 g/l NaCl; 1 g/l $NH_4Cl$; 10 ml of 0.01M $CaCl_2$ solution/l ml of 1.0M $MgSO_4$ solution/l and 2 g/l glucote, followed by sterilization by filtration (0.22 um)].

Trypticase Soy broth (5 ml) was inoculated with bacteria grown on TSAII plates, incubated for 24 hours at 30° C. and lyophilized as 100 ul aliquots in sterile 2 ml vials. Lyophilized bacteria were stored at −20° C. One vial of lyophilized bacteria was resuspended in 1 ml M9 which was then used to inoculate 500 ml of M9. After incubation at 30° C., bacteria were removed by centrifugation (30,000×g for 15 minutes at 4° C.). The supernate was concentrated to 100 ml in an Amicon DC2 (Amicon Corp., Danvers, MA) equipped with HIP5 (5,000 $M_r$ cut-off) hollow fibers. The concentrate was diluted with 500 ml water and reconcentrated to 100 ml. This procedure was repeated twice (1,500 ml water total for washing) to desalt and concentrate the supernate which was then lyophilized and stored at −20° C.

Sterility of prepared media and filtered PFF was determined by streaking TSAII plates which were then incubated for up to 14 days at 30° C. Purity of the bacteria grown in synthetic media or PFF was assessed using TSAII plates after appropriate incubation periods.

For the determination of the production of FSH-BI in various culture media was conducted as follows:

Two to 5 ml aliquots of synthetic culture media (Trypticase Soy Broth BBL Microbiology Systems; thiezlysolate Fluid Agar, BBL Microbiology Systems; Ham's F12, KC. Biological; McCoys 5A Modified Gibco; and M9;) or PFF sterilized by filtration (0.22 um filters, Millipore Corp.) were inoculated with bacteria from agar plates and inoculated at 30–33° C., typically for 48 hours. Culture media were then centrifuged at 30,000×g for 15 minutes at 4° C. to remove bacteria and the supernates were dialyzed using 6000 molecular weight cut off membranes (Spectrapor #1, Spectrum Medical Industries, Los Angeles) against water for 24 hours.

As can be seen from Table 2, FSH-BI was produced in all the tested types of culture media.

The method for detection of FSH-binding inhibition is performed as follows:

Quantitation of Binding Inhibition: Samples were tested in radioligand-receptor assays for inhibition of the binding of radioiodinated gonadotropins to receptor. Percent binding was defined as specific binding in the presence of sample divided by specific binding in the absence of sample multiplied by 100. Percent binding inhibition was then defined as 100 minus the percent binding. Specific binding was calculated as total binding less nonspecific binding. Binding inhibition was quantitated on the basis of dose ($BI_{50}$) of sample required to produce 50% inhibition of specific binding. $BI_{50}$ values were calculated from inhibition curves generated using multiple doses of sample. Additionally, all assays were monitored using inhibition curves generated by multiple doses of hormone reference preparations.

FSH assay: Radioligand-receptor assays using radioiodinated ($^{125}I$) human FSH as the radioligand and calf testis membranes as the receptor source (120 to 31,000×g pellet) were conducted as previously described (Sluss and Reichert, *Biol. Reprod.* 29: 335-341; 1983). Nonspecific binding was determined using a 300 fold molar excess of hFSH (LER-1760, 50 IU/mg). Assay performance was evaluated on the basis of specific binding/total counts added, nonspecific binding/total binding, and characteristics ($BI_{50}$ dose, slope) of binding inhibition curves generated with multiple doses of bFSH or hFSH reference preparations.

LH-BI assay: Highly purified hLH (LER-1972, 5,000 IU/mg) or hCG (CR 119, 10,000 IU/mg) were used as radioligands for these assays. Human LH was radioiodinated by a Chloramine-T procedure (Leidenberger and Reichert, *Endocrinol* 91: 901-909; 1972) and hCG was radioiodinated using the lactoperoxidase procedure described in detail previously for hFSH (Sluss et al., *Biol. Reprod.* 29: 1105-1113; 1983). Radioligand-receptor assays using rat Leydig cells as a receptor source were performed as originally described in Leidenberger and Reichert, 1972, except that 50 mM HEPES was used in place of 50 mM Tris in the assay buffer. As shown in Table 3, the dose required to inhibit binding by 50% ($BI_{50}$) was approximately 100 fold higher for $^{125}I$-hLH than for $^{125}I$-hFSH. Thus, although inhibition of $^{125}I$-hLH binding to receptor was observed, the FSH-BI is about 100 times more potent (based on mass) with respect to inhibition of $^{125}I$-FSH binding to receptor.

Deposit of Strains Useful in Practicing the Invention

A deposit of biologically pure cultures of the following strain was made with the American Type Culture Collection, 12301 Parklawn Drive, Rockville, Md. on June 6, 1986. The accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application, and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture of the same taxonomic description.

| Strain | ATCC Number |
| --- | --- |
| Serratia sp. biotype 5107763 | 53497 |

TABLE 2

Production of FSH—BI in dialyzed synthetic culture media. Percent Inhibition of $^{125}I$—hFSH binding/100 ul Medium[a]

| Medium | Sterile Control | Incubated with Serratia[b] |
| --- | --- | --- |
| Sterile PFF | 9 | 84 |
| Trypticase Soy Broth | 4 | 97 |
| Thioglycollate Fluid Agar | 8 | 93 |
| McCoy's 5A Modified | −4 | 92 |
| Ham's F12 | −6 | 93 |
| M9 | 5 | 95 |

[a]Media were dialyzed against deionized water for 24 hours at 4° C. Samples (100 ul) were assayed as described in example 4.
[b]Serratia isolated from PFF, biotype 5107763.

TABLE 3

Inhibition of a $^{125}I$—hLH and $^{125}I$—hFSH binding to receptor by FSH—BI secreted by Serratia 5107763[a]

| Replicate | $^{125}I$—hLH/Rat Leydig Cell Assay[b] $BI_{50}$ Dose | $^{125}I$—hFSH/Calf Testis Membrane[c] $BI_{50}$ Dose |
| --- | --- | --- |
| 1 | 500 ug | 2.5 ug |
| 2 | 390 ug | 3.5 ug |
| 3 | — | 2.8 ug |
| x | 445 ug | 2.9 ug |
| SD | 78 ug | 0.5 ug |

[a]FSH—BI was secreted by Serratia 5107763 incubated in 5 ml M9 medium for 48 hours at 30° C. Medium was then centrifuged to remove bacteria and dialyzed (Spectrapor #1, 6,000 $M_r$ cut-off). Dialyzed medium was assayed at multiple doses in both types of radioligand-receptor assay. $BI_{50}$ values were calculated from percent bound vs. log dose FSH—BI or standard hormone binding inhibition curves.
[b]hLH reference used was the highly purified hLH (LER 1972, 5,000 IU/ml) which was also used to prepare the $^{125}I$—hLH. $BI_{50}$ doses for this reference preparation was 5.3 ± 0.4 ng/ml.
[c]bFSH reference used was LER 1596 which was 50 times less active than the highly purified hFSH (LER 1781-2, 4,000 IU/mg) used to prepare the $^{125}I$—hFSH. The $BI_{50}$ of bFSH was 343 ± 28 ng/ml which is analogous to 6.9 ng/ml of highly purified h FSH (1781-2).

TABLE 4

FSH—BI and total protein in PFF incubated with Serratia 5107763[a].

| SAMPLE | Replicate | Percent Binding Inhibition by 100 ul dialyzed PFF | Total Protein (mg) in ul dialyzed Pff[b] |
| --- | --- | --- | --- |
| Serratia | 1 | 51.9 ± 4.2 | 2.75 ± 0.16 |
| | 2 | 50.1 ± 0.3 | 1.59 ± 0.06 |
| | 3 | 51.0 ± 1.6 | 2.52 ± 0.09 |
| | 4 | 48.5 ± 0.4 | 2.17 ± 0.02 |
| | x ± SE | 50.4 ± 0.4** | 2.79 ± 0.13 |
| Control PFF (sterile) | 1 | 11.8 ± 5.5 | 2.79 ± 1.20 |
| | 2 | 8.9 ± 2.4 | 2.74 ± 0.14 |
| | 3 | 10.9 ± 1.3 | 2.59 ± 0.09 |
| | 4 | 7.9 ± 0.2 | 2.87 ± 0.05 |
| | x ± SE | 9.9 ± 0.4 | 2.75 ± 0.03 |

[a]Stock cultures of Serratia 5107763 were tested for generation of Large $M_r$ FSH—BI using standard assay procedures as described in legend to FIG. 2. Value shown for each replicate are mean ± SD of assay duplicates for both FSH—BI and total protein determinations.
[b]Value indicated are mg total protein determined as described in Materials and Methods using Bovine Serum Albumin as the assay standard.
**Significantly different than Control PFF, $P < 0.001$

What we claim is:

1. An FSH-binding inhibitor characterized by the following features:
    (a) a molecular weight of over 6000;

(b) inactivation by heating at 60° C. for 30 minutes;
(c) inactivation by pH below 4;
(d) insolubility in either; 75% acetone; and 40% ammonium sulfate;
(e) insolubility in 80% ethanol;
(f) absence of serine protease activity; and
(g) inhibits binding of FSH; said binding inhibitor obtainable from a microorganism of the genus Serratia selected from the group consisting of Serratia Sp. ATCC 53497; *Serratia marcescens*, ATCC No. 13880; *Serratia marcescens*, ATCC No. 21074; *Serratia liquefaciens* ATCC No. 11367; *Serratia liquefacines* ATCC No. 27592; *Serratia plymuthica* ATCC No. 183 and *Serratia fonticola* ATCC No. 29844, by culturing the microorganism on a medium containing a suitable carbon source at about 30° C. for a period of 24 to 48 hours.

* * * * *